United States Patent
Maeda et al.

(10) Patent No.: US 6,884,900 B2
(45) Date of Patent: Apr. 26, 2005

(54) METHOD FOR PRODUCING FATTY ACID ALCOHOL ESTER

(75) Inventors: Yasuaki Maeda, Kawachinagano (JP); Mircea Vinatoru, Bucharest (RO); Carmen Eugenia Stavarach, Sakai (JP); Kunio Iwai, Inzai (JP); Hideki Oshige, Kawasaki (JP)

(73) Assignee: Cosmo Engineering Co., Ltd., Tokyo (JP)

( * ) Notice: Subject to any disclaimer, the term of this patent is extended or adjusted under 35 U.S.C. 154(b) by 8 days.

(21) Appl. No.: 10/678,116

(22) Filed: Oct. 6, 2003

(65) Prior Publication Data
US 2004/0159537 A1 Aug. 19, 2004

(30) Foreign Application Priority Data
Oct. 15, 2002 (JP) .................................. 2002-300920
Sep. 26, 2003 (JP) .................................. 2003-335154

(51) Int. Cl.$^7$ ................................................ C11C 3/00
(52) U.S. Cl. ..................................................... 554/169
(58) Field of Search ........................................ 554/169

(56) References Cited

PUBLICATIONS

Stavarach et al., Chemistry Letters, vol. 32, No. 8, pp. 716–717, 2003, "Conversion of vegetable oil to biodiesel using ultrasonic irradiation."*

* cited by examiner

*Primary Examiner*—Deborah D. Carr
(74) *Attorney, Agent, or Firm*—Manabu Kanesaka

(57) ABSTRACT

There is provided a method for producing fatty acid alcohol ester useful as a substitute fuel for light oil in which an ester interchange reaction between fats or oils and alcohol is carried out in a reactor 1 by applying ultrasonic irradiation at a frequency of 15 to 100 kHz and irradiation intensity of 0.5 to 20 W/cm$^2$ in the presence of a catalyst, followed by an application of ultrasonic irradiation at a frequency of 200 to 3,000 kHz and irradiation intensity of 0.5 to 20 W/cm$^2$ to the reaction product in a separation tank 4 to separate fatty acid alcohol ester and glycerol. Such ultrasonic irradiation in the separation tank 4 may be applied to an interface between fatty acid alcohol ester and glycerol.

8 Claims, 2 Drawing Sheets

METHOD FOR PRODUCING FATTY ACID ALCOHOL ESTER

BACKGROUND OF THE INVENTION

1. Field of the Invention

This invention relates to a method for producing fatty acid alcohol ester useful as a substitute fuel for light oil, and more particularly relates to a method for producing fatty acid alcohol ester together with highly valuable glycerol as a byproduct.

2. Prior Art

Due of lower ignitibility and higher pour point of such vegetable fats or oils compared with those properties of light oil, they themselves are not useful as a substitute fuel for light oil.

On the other hand, fatty acid alcohol ester prepared by reacting the vegetable fats or oils as a starting material with alcohol is considered as a hopeful biodiesel fuel oil (hereinafter referred to as BDF) from a viewpoint of measures against global warming to control an increase in carbon dioxide on the earth.

A mixture of the vegetable fats or oils with alcohol in the presence of a catalyst causes an ester interchange reaction to substantially change the vegetable fats or oils to fatty acid alcohol ester, thereby glycerol and fatty acid soap being formed as byproducts (see, JP-A No. 2000-143,586, JP-A No. 2001-524,553 and "Biodiesel Production and Quality" (2002), a leaflet of U.S. National Biodiesel Board (NBB)).

The above mentioned reaction comprises, for example, formation of fatty acid alcohol ester and glycerol as a main reaction and formation of fatty acid soap and water as a side reaction as shown in the following reaction formulas:

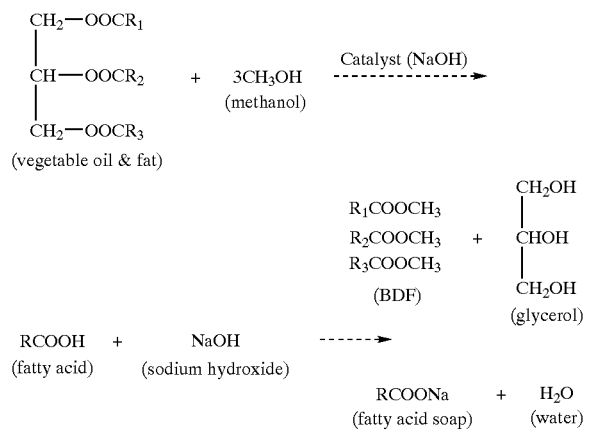

Ignitibility (cetane number) and pour point of the fatty acid alcohol ester approximate to those of light oil and thus are sufficiently useful as a diesel fuel, i.e., a substitute fuel for light oil.

As an ester interchange reaction is so slow that it takes several hours to complete the reaction at ordinary temperatures and is carried out in a reactor of larger scale, the reaction is generally accelerated by rising temperatures, which requires higher thermal energy.

Further, a limit of rise in temperature is about 50 to 60° C., although the reaction rate can be accelerated with an increase in temperature, because volatile alcohol such as methanol is used.

Furthermore, even when the reactor is equipped with an agitator or line mixer to improve its agitation effect, it takes about 30 minutes to one hour to conduct the reaction.

The above mentioned alcohol or catalyst is sometimes used in an excessive amount to accelerate the reaction, however, unreacted alcohol, residual catalyst or excessively formed fatty acid soap should be removed from the ester product in the purification process, which would require scale up of the purification facilities, make the reaction system complex and increase the plant investment or running cost.

As has been described above, conventional production technology of fatty acid alcohol ester yields ester and glycerol of inferior purity as the reaction products due to an excessive amount of alcohol as one of starting materials and catalyst used in the reaction, thereby affecting the combustibility of DBF and exhaust gas composition therefrom and disturbing an practical application thereof. If the conventional production technology is employed as it is in the purification process, an enormous production cost should be necessary.

Considering the present status of this technological field, it is inevitable to develop technology for producing and purifying fatty acid alcohol ester at a greatly reduced production cost so as to spread it as a substitute fuel for light oil.

SUMMARY OF THE INVENTION

Accordingly, it is an object of the invention to provide a method for producing and purifying fatty acid alcohol ester as a substitute fuel for light oil at a greatly reduced production cost.

BRIEF DESCRIPTION OF THE DRAWINGS

FIGS. 1(A) to 1(C) show an embodiment of this invention, in which FIG. 1(A) is a flow diagram of whole process, while FIGS. 1(B) and 1(C) are other embodiments of an ultrasonic transducer 2 arranged in a reactor 1 and a separation tank 4, respectively.

DETAILED DESCRIPTION

Figure 1A:
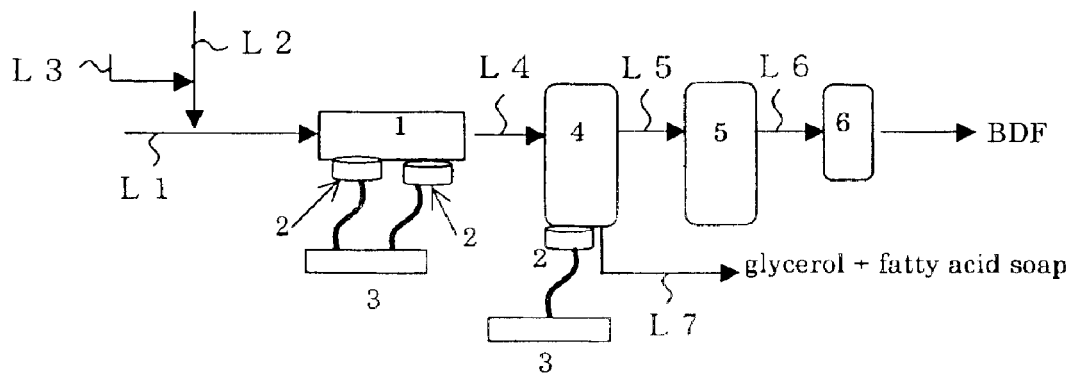

The inventors have investigated very hard to solve the above mentioned problems. First of all, in order to accelerate an ester interchange reaction described in JPH No. 2001-524,553 and to improve the reaction efficacy, a static mixer was used to cause a strong dynamic turbulent flow within the reaction region, so that a mixture interface in the reactor is expanded to promote the reaction through emulsification. However, it was found in such a modified procedure of the disclosure that the reaction product, byproducts and unreacted materials are emulsified, which arouses another new problem of difficulty in separation.

On the other hand, the reaction described in JP-A No. 2000-143,586 was conducted under a supercritical or subcritical condition to accelerate the reaction and improve the reaction efficacy. This process was costly and impractical.

It was also found that electromagnetic irradiation such as radiation or microwave exposure and, in addition, an undesirably high temperature in the reaction field are hardly used in this concern from a viewpoint of safety.

The following information has been finally obtained as a result of further investigations.

(1) Ultrasonic irradiation to liquid at a specific frequency causes cavitation in the liquid by a function of compressional wave, which accelerates the mass transfer, while the reaction is accelerated due to local rise in temperature and pressure within the cavitation thus formed. When these acceleration effects are applied to the reaction starting from vegetable fats or oils and alcohol in the presence of a catalyst, the ester interchange rate can be remarkably increased.

(2) Ultrasonic irradiation at a specific frequency accelerates the phase separation. When such an effect is applied to the mixture of fatty acid alcohol ester and glycerol formed by the ester interchange reaction, the fatty acid alcohol ester of high purity can be separated from glycerol rapidly.

This invention is based on the above mentioned information and characterized in that an ester interchange reaction between oils or fats and alcohol is carried out in the presence of a catalyst by ultrasonic irradiation at a frequency of 15 to 100 kHz and irradiation intensity of 0.5 to 20 W/cm$^2$ in a method for producing fatty acid alcohol ester.

Further, this invention is characterized in that fatty acid alcohol ester is separated from glycerol by ultrasonic irradiation to a product of ester interchange reaction at a frequency of 200 to 3,000 kHz and irradiation intensity of 0.5 to 20 W/cm$^2$.

The ultrasonic irradiation for separating the ester and glycerol is preferably done to an interface between them.

In other words, this invention is an application of sonochemical technology, in which a reaction in liquid is accelerated by ultrasonic irradiation to plural starting materials of low reaction rate at a specific frequency, while liquid-liquid separation of products having low gravity difference is accelerated by ultrasonic irradiation at a specific frequency.

Starting fats or oils used in the invention include those of vegetable origins such as rapeseed oil, soybean oil, olive oil, coconut oil and palm oil as well as animal fats or oils and fish oils. Waste fats or oils thereof may also be used. These fats or oils may either be used independently or as a combination of two or more of them.

A starting alcohol of the invention includes either methanol or ethanol, which may be used independently or as their mixture of suitable mixing ratio.

An insufficient amount of the starting alcohol not only decreases the reaction rate of ester interchange but promotes the reaction insufficiently, while an excess thereof makes it difficult to separate the unreacted alcohol in the purification process. Thus, a suitable amount of the starting alcohol is stoichiometrically 1 to 1.3 times, preferably 1 to 1.2 times and more preferably 1 to 1.17 times of fats or oils.

According to the cited conventional procedures, the starting alcohol is used in such a larger amount as 1.5 times of stoichiometry or more, which causes problems in the purification process. According to the invention, however, ultrasonic irradiation is applied to the reaction under a specific condition which causes cavitation in liquid as described above, thereby promoting the ester interchange reaction sufficiently within a short period of time, even when the starting alcohol is used stoichiometrically or in a smaller amount as 1.17 times of stoichiometry.

A catalyst used in the invention includes either sodium hydroxide or potassium hydroxide, which may be used independently or as their mixture of suitable mixing ratio.

An insufficient amount of the catalyst not only decreases the reaction rate of ester interchange but promotes the reaction insufficiently, while an excess thereof makes it difficult to separate the catalyst in the purification process. Preferably, the catalyst is used in an amount of 0.2 to 1.5% by weight of fats or oils in the invention.

According to the cited conventional procedures, the catalyst is used in such a larger amount as 2 to 3% by weight of fats or oils, which causes problems in the purification process. According to the invention, however, ultrasonic irradiation is applied to the reaction under a specific condition which causes cavitation in liquid as described above, thereby promoting the ester interchange reaction sufficiently within a short period of time, even when the catalyst is used in a smaller amount as 0.2 to 1.5% by weight.

According to the invention, ultrasonic irradiation is applied to a mixture of starting fats or oils, a starting alcohol and a catalyst at a frequency of 15 to 100 kHz, preferably 20 to 40 kHz and irradiation intensity of 0.5 to 20 W/cm$^2$.

Ultrasonic irradiation causes cavitation in the mixed liquid under the above mentioned condition, thereby promoting mass transfer (of the fats or oils and the alcohol), while the reaction is accelerated due to local rise in temperature and pressure to remarkably increase the reaction rate of ester interchange.

Conventionally, it takes a long period of time as 5 to 10 hours at ordinary temperatures and 30 minutes to one hour with heating to complete the ester interchange reaction, while the reaction of the invention can be completed within only 10 to 20 minutes at ordinary temperatures.

Further, as the ester interchange reaction is thus accelerated, it is possible to control formation of fatty acid soap to a low level, which should be removed from the reaction system as impurities.

Ultrasonic irradiation at a frequency below 15 kHz and irradiation intensity below 0.5 W/cm$^2$ is not enough to promote mass transfer due to cavitation or accelerate the reaction, and similar irradiation at those levels over 100 kHz and 20 W/cm$^2$ reduces the mass transfer promotion and lower the reaction rate.

Ultrasonic irradiation under a preferred condition as described above may be conducted at ordinary temperatures and pressure without heating, while agitation or mixing by means of, for example, an agitator is not always necessary.

Ultrasonic irradiation may be carried out from either part of the reactor such as side-, bottom- or top-surface or internal center thereof, or from whole of these parts, although irradiation from the side or the bottom is preferable. An arrangement of ultrasonic irradiation means (ultrasonic transducer) may be focused to one point on the side or bottom surface, or distributed homogeneously in several points thereon.

The ester interchange reaction may be carried out continuously in a continuous reactor or a discontinuously in a batch-wise reactor.

When the ester interchange reaction is conducted in a manner as described above, there is formed a reaction product comprising fatty acid alcohol ester, glycerol and fatty acid soap which further contains unreacted starting materials and a catalyst as a mixture.

According to the invention, ultrasonic irradiation is then applied to the reaction product at a frequency of 200 to 3,000 kHz and irradiation intensity of 0.5 to 20 W/cm$^2$, thereby fatty acid alcohol ester of high purity being rapidly separated from glycerol.

At a frequency below 200 kHz, such ultrasonic irradiation causes mixing of the product rather than separation thereof and reduces its separating purification efficacy, while at a frequency over 3,000 kHz, the ultrasonic irradiation effect is saturated. Aggregation of droplets is promoted insufficiently at irradiation intensity below 0.5 W/cm$^2$, while there occurs mixing of the product rather than separation thereof at irradiation intensity over 20 W/cm², which reduces the separating purification efficacy.

When ultrasonic irradiation is applied to an interface between fatty acid alcohol ester and glycerol, aggregation of their droplets in the vicinity of the interface is promoted to further improve the separation efficacy.

As the fatty acid alcohol ester is separated in a highly purified state, a slight amount of residual alcohol, catalyst and fatty acid soap can be removed therefrom by simply washing with water, etc. to yield the ester as a product.

On the other hand, the fatty acid soap is transferred to a glycerol portion, which is then subjected to treatments in the adjacent process, such as neutralization, removal of the soap by salting out, distillation, adsorptive removal of impurities and redistillation, to yield glycerol of high purity.

Effects of the Invention

According to the invention, fatty acid alcohol ester as a biodiesel fuel oil can be produced effectively within a short period of time under a condition of ordinary temperatures and ordinary pressure without agitation or mixing by an agitator or other means.

An amount of alcohol as a secondary starting material and that of a catalyst can be controlled to minimize due to improvement in the reaction efficacy, while formation of fatty acid soap, which should be removed as impurities, is also inhibited.

Furthermore, according to the invention, fatty acid alcohol ester of high purity can be separated and purified from a mixture thereof with glycerol formed by the ester interchange reaction under a condition of ordinary temperatures and ordinary pressure within a short period of time.

When such an almost impurity-free fatty acid alcohol ester is used as a biodiesel fuel oil for a diesel engine automobile, a soot content in the exhaust gas is reduced to one third compared with that of light oil, while carcinogenic benzpyrene is scarcely present in PM (particular matter) and a nitrogen oxides content thereof is reduced to about 75% compared with that of light oil.

A sulfur oxides content of the product is also low because fats or oils of vegetable origin are used in the invention as a starting material of low sulfur content.

As has been described above, the invention provides an environmentally friendly substitute fuel for light oil at a low cost and, accordingly, is quite effective as a measure against global warming.

PREFERRED EMBODIMENTS

Referring now to the drawings, an embodiment of the invention will be detailed.

FIG. 1(A) is a flow diagram of whole process, in which numeral 1 designates an ester interchange reactor 1. A starting fat or oil is introduced into the reactor through a line L1, to which a starting alcohol and a catalyst are supplied to form a mixture thereof through lines L2 and L3, respectively.

The reactor 1 is a unit of ultrasonic type, to the bottom surface of which plural ultrasonic transducers 2 are arranged, although only two of them are shown in FIG. 1(A) for the sake of convenience. These ultrasonic transducers 2 are connected to an ultrasonic generator 3, which may be used plurally but only one generator is shown in FIG. 1(A) for the sake of convenience.

An arrangement of the ultrasonic transducers 2 is not limited to the bottom surface of the reactor 1. Further, the ultrasonic transducers 2 may be arranged to the side surface, or the top surface if the reactor 1 is completely filled with the starting liquid mixture, and they may also be arranged to all over these surfaces or to the inside surface (inner wall surface) or the outside surface (outer wall surface) of the reactor 1.

Figure 1B:
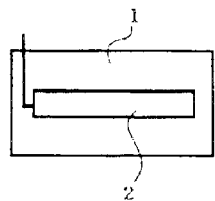

Furthermore, the ultrasonic transducers 2 may be arranged inside of the reactor 1 coaxially thereto as shown in FIG. 1(B).

The reactor 1 may be in the shape of a rectangular parallelepiped, a cylinder or any others.

After the ester interchange reaction by ultrasonic irradiation is completed under a predetermined condition in the reactor 1, the thus reacted liquid mixture is supplied to a separation tank 4 through a line L4.

The separation tank 4 is also an ultrasonic type, to the bottom surface of which plural ultrasonic transducers 2 are arranged, although only one of them is shown in FIG. 1(A) for the sake of convenience. These ultrasonic transducers 2 are connected to the ultrasonic generator 3, which may be used plurally but only one of them is shown in FIG. 1(A) for the sake of convenience.

An arrangement of the ultrasonic transducers 2 is not limited to the bottom surface of the separation tank 4 but may be on the side or top surface. They may also be arranged to all over these surfaces or to the inside surface (inner wall surface) or the outside surface (outer wall surface) of the separation tank 4.

Figure 1C:
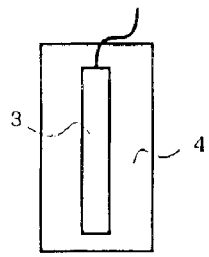

Further, the ultrasonic transducers 2 may be arranged inside of the separation tank 4 coaxially thereto as shown in FIG. 1(C).

The separation tank 4 may be shaped in a rectangular parallelepiped, a cylinder or any other body.

After the separating operation by ultrasonic irradiation is completed under a predetermined condition in the separation tank 4, an upper layer comprising fatty acid alcohol ester is supplied to a washing tank 5 through a line L5. After the residual alcohol, catalyst and fine particles of fatty acid soap are removed from the crude product by water washing, etc., the fatty acid alcohol ester is taken out of the washing tank 5 and kept in a product tank 6 ready for use as a biodiesel fuel oil (BDF), i.e., a substitute for light oil.

A lower layer comprising a liquid mixture of glycerol and fatty acid soap in the separation tank 4 is taken out through a line L7 and supplied to a separation process (not shown), where the liquid mixture is, for example, neutralized and then subjected to a salting out treatment by addition of salt to remove fatty acid soap, thereby yielding a glycerol product. Alternatively, the liquid mixture is distilled to purify glycerol after the fatty soap is removed, which is diluted with water and treated with active carbon to further remove impurities, followed by redistillation for the purpose of further purification to yield a glycerol product of high purity.

Such glycerol as a byproduct of BDF is quite valuable in various fields.

Figure 2:
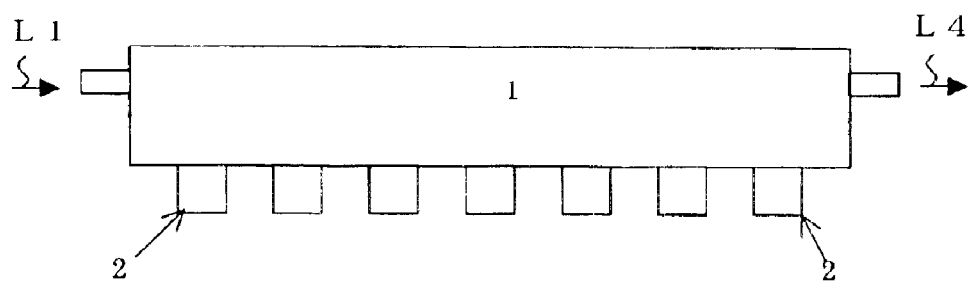
FIG. 2 is a sectional view of a reactor shown in FIGS. 1(A) and 1(B) according to further another embodiment.

In FIG. 2, a continuous reactor 1 is used instead of the reactor 1 shown in FIG. 1(A), in which each part of the same symbol or numeral functions similarly as shown in FIG. 1(A).

The continuous reactor 1 shown in FIG. 2 may be shaped in a rectangular parallelepiped, a cylinder or a polygonal body in section, extending longer in the direction of liquid flow, and is provided with plural ultrasonic transducers 2 on the bottom surface. Similarly as shown in FIGS. 1(A) and 1(B), an arrangement of the ultrasonic transducers 2 is not limited to the bottom surface of the separation tank 4 but may be on the side or top surface. They may also be arranged to all over these surfaces or to the inside surface (inner wall surface) or the outside surface (outer wall surface) of the reactor 1. Further, the ultrasonic transducers 2 may be arranged inside of the continuous reactor 1 coaxially thereto similarly as shown in FIG. 1(B).

The other devices and lines used in FIG. 2 may be arranged similarly as shown in FIGS. 1(A) to 1(C).

According to the embodiment shown in FIG. 2, fatty acid alcohol ester is produced continuously.

Figure 3:
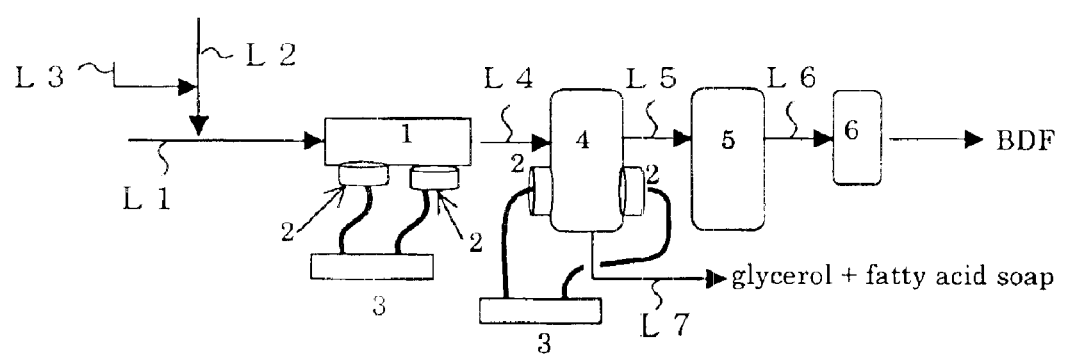
FIG. 3 is a flow diagram of whole process according to yet another embodiment.

In FIG. 3, there is shown another embodiment in which an arrangement of ultrasonic transducers 2 in a separation tank 4 is different from that of in FIGS. 1(A) to 1(C). Each part of the same symbol or numeral in FIG. 3 functions similarly as shown in FIGS. 1(A) to 1(C).

The ultrasonic transducers 2 are arranged to the side surfaces of the separation tank 4 in FIG. 3 so that they locate on the surface close to the interface between fatty acid alcohol ester and glycerol.

When the separation tank 4 is a continuous type in which the interface between fatty acid alcohol ester and glycerol can be controlled to keep a nearly constant level by, for example, taking out the ester and/or glycerol, the ultrasonic transducers 2 may be arranged sildably on the side surface of the separation tank 4 in the direction of height, although they may be fixed thereon.

EXAMPLE 1 AND COMPARATIVE EXAMPLE 1

According to a process shown in FIG. 3, the ester interchange reaction was carried out under a condition shown in Table 1 below using a commercially available rapeseed oil as a starting oil, methanol as an alcohol and sodium hydroxide as a catalyst. The result of Example 1 is shown in Table 1.

Further, for the purpose of comparison, the ester interchange reaction was carried out conventionally under a condition shown in Table 1 without applying ultrasonic irradiation. The result of Comparative example 1 is also shown in Table 1.

TABLE 1

|  | Ex. 1 | Comparative Ex. 1 |
|---|---|---|
| Fat or oil | rapeseed oil | rapeseed oil |
| Reaction temperature and pressure | ordinary | ordinary |
| Ultrasonic frequency | 28 kHz | 0 |
| Ultrasonic intensity | 6 W/cm$^2$ | 0 |
| Reaction time | 15 min. | 5 to 10 hrs. |
| Agitation | no | yes |
| Quantity of catalyst (wt % to fat or oil) | 0.5 wt % | 3.0 wt % |
| Quantity of alcohol (wt % to fat or oil) | 15 wt % | 20 wt % |
| Separation temperature and pressure | ordinary | ordinary |
| Ultrasonic frequency | 600 kHz | 0 |
| Ultrasonic intensity | 6 W/cm$^2$ | 0 |
| Irradiation time | 5 min. | 0 |
| Static separation time | 10 min. | 5 to 10 hrs. |
| Yield of ester*[1] | 98 wt % | 90 wt % |
| Yield of glycerol layer*[1] | 17 wt % | 33 wt % |

TABLE 1-continued

|  | Ex. 1 | Comparative Ex. 1 |
|---|---|---|
| Purity of glycerol | relatively high | considarable impurities |
| Yield of soap*[1] | ≦1 wt % | 2 to 3 wt % |

*[1]wt % to fat or oil

EXAMPLES 2 TO 4

According to a process shown in FIG. 3, the ester interchange reaction was carried out under a condition shown in Table 2 below using a commercially available rapeseed oil as a starting oil, methanol as an alcohol and potassium hydroxide as a catalyst. The result of Examples 2 to 4 is shown in Table 2.

TABLE 2

|  | Ex. 2 | Ex. 3 | Ex. 4 |
|---|---|---|---|
| Fat or oil | rapeseed oil | rapeseed oil | rapeseed oil |
| Reaction temperature and pressure | ordinary | ordinary | ordinary |
| Ultrasonic frequency | 40 kHz | 40 kHz | 40 kHz |
| Ultrasonic intensity | 0.5 W/cm$^2$ | 0.5 W/cm$^2$ | 0.5 W/cm$^2$ |
| Reaction time | 30 min. | 30 min. | 30 min. |
| Agitation | no | no | no |
| Quantity of catalyst (wt % to fat or oil) | 0.5 wt % | 0.5 wt % | 0.5 wt % |
| Quantity of alcohol (wt % to fat or oil) | 20 wt % | 20 wt % | 20 wt % |
| Separation temperature and pressure | ordinary | ordinary | ordinary |
| Ultrasonic frequency | 1500 kHz | 35 kHz | 0 |
| Ultrasonic intensity | 10 W/cm$^2$ | 10 W/cm$^2$ | 0 |
| Irradiation time | 10 sec. | 10 sec. | 0 |
| Static separation time | 20 min. | 3 hrs | 3 hrs . . . |
| Yield of ester*[1] | 98 wt % | 98 wt % | 98 wt % |
| Yield of glycerol layer*[1] | 22 wt % | 22 wt % | 22 wt % |
| Yield of soap*[1] | ≦1 wt % | ≦1 wt % | ≦1 wt % |

*[1]wt % to fat or oil

In Example 3, ultrasonic irradiation was conducted at a lower frequency than that of claimed in claim 2, thereby causing a mixed situation rather than separation. It took 3 hours, or 9 times compared with Example 2, for static separation to obtain a similar result of separating purification as that of Example 2.

In Example 4, separating purification was conducted only by static separation without applying ultrasonic irradiation. It also took such a longer time as 3 hours as similarly as Example 3.

EXAMPLES 5 AND 6

According to a process shown in FIG. 3, the ester interchange reaction was carried out under a condition shown in Table 3 below using a commercially available palm oil as a starting oil, methanol as an alcohol and potassium hydroxide as a catalyst. The result of Examples 5 and 6 is shown in Table 3.

TABLE 3

|  | Ex. 5 | Ex. 6 |
|---|---|---|
| Fat or oil | palm oil | palm oil |
| Reaction temperature and pressure | 50° C. ordinary | 50° C. ordinary |

TABLE 3-continued

|  | Ex. 5 | Ex. 6 |
| --- | --- | --- |
| Ultrasonic frequency | 40 kHz | 40 kHz |
| Ultrasonic intensity | 0.5 W/cm$^2$ | 0.5 W/cm$^2$ |
| Reaction time | 30 min. | 30 min. |
| Agitation | no | no |
| Quantity of catalyst (wt % to fat or oil) | 0.5 wt % | 0.5 wt % |
| Quantity of alcohol (wt % to fat or oil) | 20 wt % | 20 wt % |
| Separation temperature and pressure | ordinary | ordinary |
| Ultrasonic frequency | 1500 kHz | 0 |
| Ultrasonic intensity | 10 W/cm$^2$ | 0 |
| Irradiation time | 5 min. | 0 |
| Static separation time | 1 hr. | 8 hrs . . . |
| Yield of ester*[1] | 96 wt % | 96 wt % |
| Yield of glycerol layer*[1] | 24 wt % | 24 wt % |
| Yield of soap*[1] | ≦1 wt % | ≦1 wt % |

*[1]wt % to fat or oil

In Example 6 in which palm oil was used as starting oil, separating purification was conducted only by static separation without applying ultrasonic irradiation. It took 8 hours, which was more than 7 times compared with the time period required in Example 5, i.e., an hour and 5 minutes.

EXAMPLE 7

The ester interchange reaction was carried out in a similar manner as described in Example 1 except that the ultrasonic transducers 2 of the separation tank 4 are arranged to meet the interface between fatty acid alcohol ester and glycerol. The result of Example 7 is shown in Table 4.

TABLE 4

|  | Ex. 7 |
| --- | --- |
| Fat or oil | rapeseed oil |
| Reaction temperature and pressure | ordinary |
| Ultrasonic frequency | 28 kHz |
| Ultrasonic intensity | 6 W/cm$^2$ |
| Reaction time | 15 min. |
| Agitation | no |
| Quantity of catalyst (wt % to fat or oil) | 0.5 wt % |
| Quantity of alcohol (wt % to fat or oil) | 15 wt % |
| Separation temperature and pressure | ordinary |
| Ultrasonic frequency | 600 kHz |
| Ultrasonic intensity | 6 W/cm$^2$ |
| Irradiation time | 3 min. |
| Static separation time | 3 min. |
| Yield of ester*[1] | 98 wt % |
| Yield of glycerol layer*[1] | 17 wt % |
| Yield of soap*[1] | ≦1 wt % |

*[1]wt % to fat or oil

It has been found that such ultrasonic irradiation to the interface between fatty acid alcohol ester and glycerol in the separation tank 4 further improves the separating purification efficacy, shortens both of the irradiation time and the static separation time compared with Example 1 and results in effects equivalent to those results obtained in Example 1.

APPLICABILITY OF THE INVENTION

This invention provides an effective method for producing fatty acid alcohol eater which is practically useful as a substitute fuel for light oil of high purity at high efficacy and at a low cost.

Further, this invention provides an effective method for separating and purifying glycerol of high purity and valuable applicability as a byproduct at high efficacy and at a low cost.

What is claimed is:

1. A method for producing fatty acid alcohol ester by conducting an ester interchange reaction between fats or oils and alcohol by applying ultrasonic irradiation at a frequency of 15 to 100 kHz and irradiation intensity of 0.5 to 20 W/cm$^2$ in the presence of a catalyst.

2. A method for producing fatty acid alcohol ester claimed in claim 1 in which a product is subjected to ultrasonic irradiation at a frequency of 200 to 3,000 kHz and irradiation intensity of 0.5 to 20 W/cm$^2$ to separate fatty acid alcohol and glycerol.

3. A method for producing fatty acid alcohol ester claimed in claim 2 in which ultrasonic irradiation is applied to an interface between fatty acid alcohol ester and glycerol.

4. A method for producing fatty acid alcohol ester claimed in claim 1 in which an amount of alcohol to be used is stoichiometrically 1 to 1.3 times of fats or oils.

5. A method for producing fatty acid alcohol ester claimed in claim 1 in which an amount of a catalyst to be used is 0.2 to 1.5% by weight of fats or oils.

6. A method for producing fatty acid alcohol ester claimed in claim 1 in which fats or oils are at least rapeseed oil, olive oil, coconut oil, palm oil, animal fats or oils, fish oil and waste oils thereof.

7. A method for producing fatty acid alcohol ester claimed in claim 1 in which alcohol is methanol and/or ethanol.

8. A method for producing fatty acid alcohol ester claimed in claim 1 in which a catalyst is sodium hydroxide and/or potassium hydroxide.

* * * * *